(12) United States Patent
Yokoyama et al.

(10) Patent No.: US 9,025,153 B2
(45) Date of Patent: *May 5, 2015

(54) PROCESS FOR PREDICTING DEGREE OF MOTTLING IN COATING COMPOSITIONS BY WET COLOR MEASUREMENT

(71) Applicant: Axalta Coating Systems IP Co., LLC, Wilmington, DE (US)

(72) Inventors: Ayumu Yokoyama, Wallingford, PA (US); Rajesh Gopalan Saliya, Philadelphia, PA (US); Anthony Moy, Garnet Valley, PA (US); Allan Blase Joseph Rodrigues, Bloomfield Hills, MI (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 245 days.

This patent is subject to a terminal disclaimer.

(21) Appl. No.: 13/669,803

(22) Filed: Nov. 6, 2012

(65) Prior Publication Data

US 2013/0141727 A1   Jun. 6, 2013

Related U.S. Application Data

(60) Provisional application No. 61/560,503, filed on Nov. 16, 2011.

(51) Int. Cl.
   *G01N 21/55*   (2014.01)

(52) U.S. Cl.
   CPC ..................................... *G01N 21/55* (2013.01)

(58) Field of Classification Search
   CPC ................ G01J 3/46; G01J 3/50; G01J 3/02; G01J 3/463; G01J 3/501; G01J 3/10; G01N 21/255; G01N 21/25; G01N 21/251; G01N 21/57; G01N 21/55; G01N 21/4738; G01N 2021/8427; G01N 33/52; G01N 2021/7773
   USPC ........... 356/402, 425, 407, 73, 445, 319, 326, 356/421, 320, 612; 250/226, 459.1, 214 R, 250/339.07
   See application file for complete search history.

(56) References Cited

U.S. PATENT DOCUMENTS 4,936,685 A * 6/1990 Taylor et al. ................... 356/409

(Continued)

FOREIGN PATENT DOCUMENTS

| JP | H09318448 A | 12/1997 |
| JP | 2007278949 A | 10/2007 |

(Continued)

OTHER PUBLICATIONS

ISA KIPO, International Search Report and Written Opinion for Application No. PCT/US2012/064331, dated Mar. 11, 2013.

(Continued)

*Primary Examiner* — Tarifur Chowdhury
*Assistant Examiner* — Mohamed Amara
(74) *Attorney, Agent, or Firm* — Ingrassia Fisher & Lorenz, P.C.

(57) ABSTRACT

The process includes measuring flops of a layer of the coating composition applied over a test substrate of a mottling prediction device of the present invention at the start and then after a desired time interval. A delta flop is determined by subtracting from the flop at the start from that after the desired time interval and a degree of mottling of a coating resulting from the layer is visually assessed. The process is repeated with varying amounts of one or more rheology additives added to the composition and the degree of mottling vs. delta flop is plotted on a graph and then by using a curve fitting equation, a mottling prediction curve is obtained. By measuring the delta flop of a wet layer of a target coating composition, the degree of mottling in the target coating composition can then be predicted by using the mottling prediction curve.

13 Claims, 3 Drawing Sheets

(56) References Cited

U.S. PATENT DOCUMENTS

| | | | |
|---|---|---|---|
| 4,966,455 A * | 10/1990 | Avni et al. | 356/73 |
| 5,282,382 A * | 2/1994 | Fiore et al. | 73/82 |
| 5,974,160 A * | 10/1999 | Shiratori et al. | 382/112 |
| 7,184,177 B2 * | 2/2007 | Trelewicz et al. | 358/3.06 |
| 8,752,502 B2 * | 6/2014 | Eriksson et al. | 118/672 |
| 2004/0220773 A1* | 11/2004 | Nonogaki et al. | 702/183 |
| 2004/0252883 A1* | 12/2004 | Johansson et al. | 382/162 |

FOREIGN PATENT DOCUMENTS

| | | |
|---|---|---|
| KR | 20110010439 A | 2/2011 |
| WO | 2004111587 A1 | 12/2004 |

OTHER PUBLICATIONS

ISA KIPO, International Preliminary Report on Patentability for Application No. PCT/US2012/064331, dated May 20, 2014.

* cited by examiner

PROCESS FOR PREDICTING DEGREE OF MOTTLING IN COATING COMPOSITIONS BY WET COLOR MEASUREMENT

CROSS-REFERENCE TO RELATED APPLICATION

This application claims priority under 35 U.S.C. §119 from U.S. Provisional Application Ser. No. 61/560,503, filed Nov. 16, 2011, which is hereby incorporated by referenced in its entirety.

FIELD OF INVENTION

The present invention is directed to a process of predicting degree of mottling exhibited by a coating composition. The process is more particularly directed to a quality assurance process that predicts on a real time basis the degree of mottling exhibited by automotive OEM and refinish paints while such paints are being manufactured.

BACKGROUND OF INVENTION

Uneven distribution of the particulate content in paint can cause mottling, also known as striping, banding, shadowing, flooding, floating, misting, precipitation, blooming, bloom, or bleaching. Mottling typically occurs in metallic paints, when the flakes float together to produce a spotty or striped appearance in a coating resulting from such a paint. The foregoing defect can be minimized by adjusting the rheology of the paint such that aggregation or settling of flakes and/or pigments in the paint is minimized. Typically, rheology additives, such as BYK®-411 rheology additive supplied by BYK USA Inc. of Wallingford, Conn. are well suited for this purpose. Such rheology additives are added during the manufacture of the paint to control the in-can and application viscosities of the paint. However, if too much of these rheology additives are added, then coating defects, such as fish eye, cratering or orange peel appearance can result. If too little of these rheology additives are added, then the aforedescribed mottling defect can occur. Thus, it is critical for the paint manufacturer to be able to predict the degree of mottling that can result in paint being manufactured.

Typically during the manufacturing of coating compositions, such as flake containing automotive OEM or refinish paints, from time to time, an aliquot of such coating compositions being manufactured is taken, applied as a layer of desired thickness over a test substrate, dried and/or cured into a coating and its degree of mottling acceptability is assessed visually. The flop is defined in ASTM E284. The process parameters are then adjusted and the aforedescribed testing procedure is repeated until the adjusted coating composition meets the desired degree of mottling.

The aforementioned testing procedure is not only time consuming and cumbersome but it also results in frequent interruptions in the manufacturing process. As a result, the batch-to-batch quality of the resulting coating compositions can be detrimentally affected. Therefore, a need exists to develop a process that could predict the degree of mottling in a coating that would result from a coating composition while it is still being manufactured such that the manufacturing process could be readily adjusted on a real time basis to attain the desired degree of mottling.

STATEMENT OF INVENTION

The present invention is directed to a process for predicting degree of mottling in a target coating composition comprising:

(a) adding to a vessel of a flake prediction device a $S_0$ coating composition;

(b) dispensing from an opening in said vessel said $S_0$ coating composition over a test substrate to produce a $L_0$ layer of a substantially uniform thickness thereon;

(c) projecting on said $L_0$ layer a beam of light of a preset intensity at preset angles of incidence from a light source;

(d) measuring $B_0$ flop of said beam reflected from said $L_0$ layer at preset angles of reflectance by an optical measurement instrument;

(e) measuring $B_{H0}$ flop of said beam reflected from said $L_0$ layer at preset angles of reflectance by said optical measurement instrument after a desired time interval;

(f) producing a $C_0$ coating from said $S_0$ coating composition;

(g) assessing a degree of mottling $Y_0$ of said $C_0$ coating;

(h) repeating said steps (a) through (g) for $S_1$ to $S_n$ coating compositions respectively comprising $F_1$ to $F_n$ parts by weight of one or more rheology additives based on 100 parts by weight of said $S_1$ to $S_n$ coating compositions to determine $B_1$ to $B_n$ flops and $B_{H1}$ to $B_{Hn}$ flops of $L_1$ to $L_n$ layers after said desired time interval, respectively, and degree of mottling $Y_1$ to $Y_n$ of $C_1$ to $C_n$ coatings, respectively wherein n ranges from 1 to 100;

(i) subtracting said $B_{H0}$ to $B_{Hn}$ flops from said $B_0$ to $B_n$ flops of said $L_0$ to $L_n$ layers, respectively to determine $\Delta B_0$ to $\Delta B_n$ flops;

(j) storing said $B_0$ to $B_n$ flops, said $B_{H0}$ to $B_{Hn}$ flops, said $\Delta B_0$ to $\Delta B_n$ flops and said degree of mottling $Y_0$ to $Y_n$ in a computer usable storage medium of a computer;

(k) locating intersecting points on a graph where said $\Delta B_0$ to $\Delta B_n$ flops of said $L_0$ to $L_n$ layers on X-axis of said graph intersect with said degree of mottling $Y_0$ to $Y_n$ on Y-axis of said graph;

(l) using a curve fitting equation to produce a degree of mottling prediction curve on said graph;

(i) dispensing on said test substrate a $L_T$ layer of said substantially uniform thickness of a target coating composition from said vessel wherein said target coating composition contains said flakes;

(j) projecting on said $L_T$ layer a beam of light at said preset intensity and at said preset angles of incidence from said light source;

(k) measuring $B_T$ flop of said beam reflected from said $L_T$ layer at said preset angles of reflectance by said optical measurement device;

(l) measuring $B_{HT}$ flop of said beam reflected from said $L_T$ layer at preset angles of reflectance by said optical measurement instrument after said desired time interval;

(m) subtracting said $B_{HT}$ flop from said $B_T$ flop of said $L_T$ layer to determine $\Delta B_T$ flop;

(l) locating said $\Delta B_T$ flop of said $L_T$ layer on said X-axis of said graph;

(n) locating an intersecting point on said degree of mottling prediction curve that intersects with said $\Delta B_T$ flop on said X-axis of said graph; and (p) predicting degree of mottling of said target composition by locating $Y_T$ on said Y-axis of said graph that intersects with said intersecting point on said degree of mottling prediction curve that intersects with said $\Delta B_T$ on said X-axis of said graph.

DETAILED DESCRIPTION OF PREFERRED THE EMBODIMENT

As defined herein:

"Flakes" means conventional metallic flakes, such as aluminum flakes used in coating compositions that exhibit flop. Flakes can also include conventional interference flakes, inorganic flakes, organic flakes or a combination thereof.

"Coating composition" means a coating composition that contains flakes that provide lustrous appearance, i.e., flop, to a coating composition applied over a substrate, such as an automotive body, bumper or a fender. By "flop" is meant the visual change in brightness or lightness of the flake, such as metallic aluminum flake, with a change in viewing angle, that is, a change from 15 degrees to 110 degrees from a specular angle. The greater the visual change from light to dark appearance, the higher the flop. The flop accentuates the lines and curves of an automobile; therefore, it is very important in achieving this sought-after appearance of the coating. Automotive coating compositions containing metallic flakes, such as aluminum flakes are generally utilized to obtain the glossy lustrous appearance which is characteristically sought. In a typical coating composition, various components of a coating composition, such as pigments, flakes, binder polymers, solvents, rheology additives etc, are mixed and sometimes ground in ball mills.

Applicants have unexpectedly discovered that a flop of a layer from a coating composition in its wet state when measured can directly correlate to the degree of mottling that can result when such a layer dries and/or cures into a coating. However, since the optically proprieties of a wet layer of a coating composition continuously changes due to evaporation of solvent from and/or crosslinking of the wet layer, it is very difficult to correlate such wet optical property measurements to the degree of mottling in a coating that results from such a layer once it dries and/or cures into a coating. The process and the device of the present invention provide a solution to attaining the aforedescribed correlation.

Figure 1:
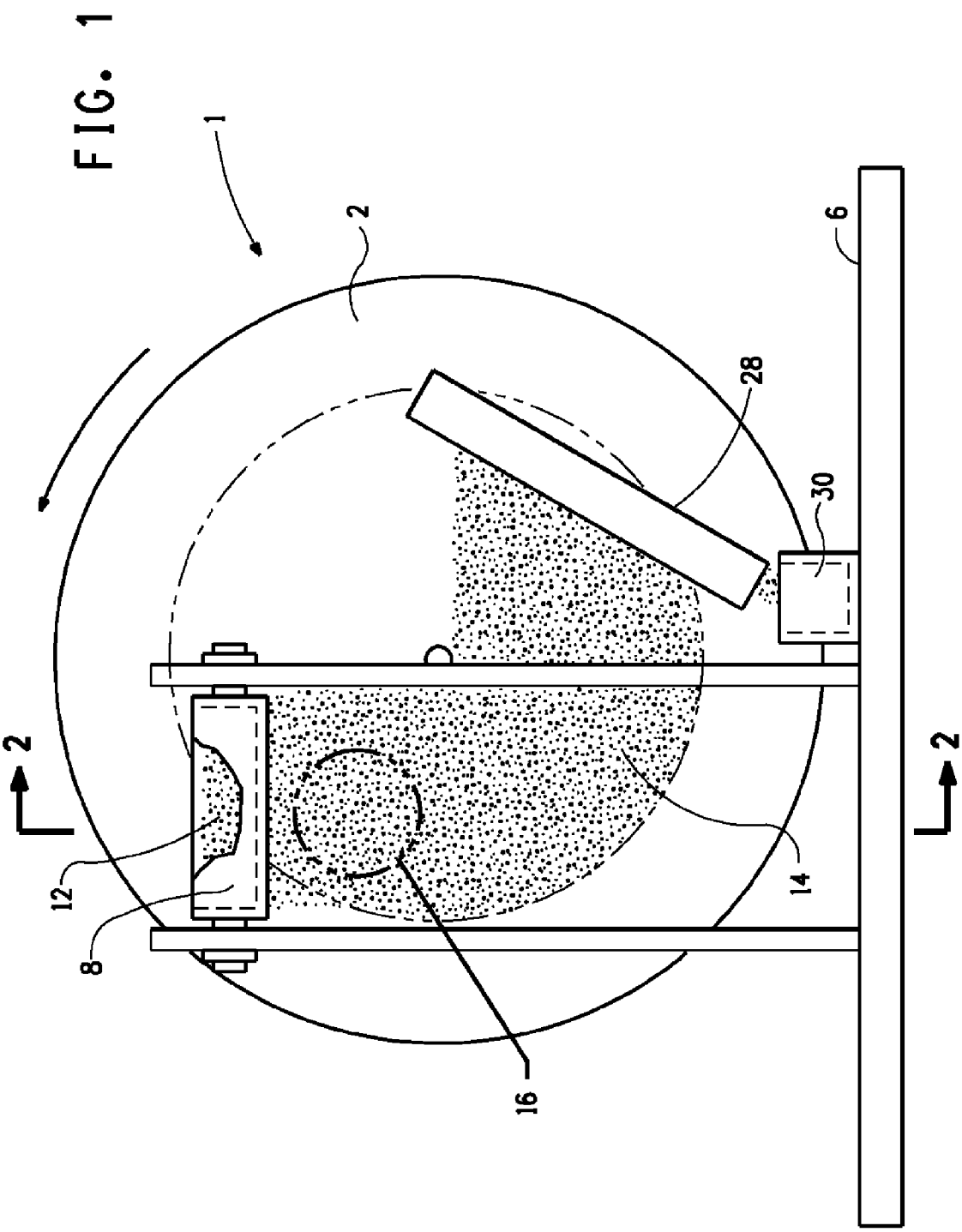
FIGS. 1 and 2 illustrate one of the embodiments of a mottling prediction device of the present invention.
Figure 2:
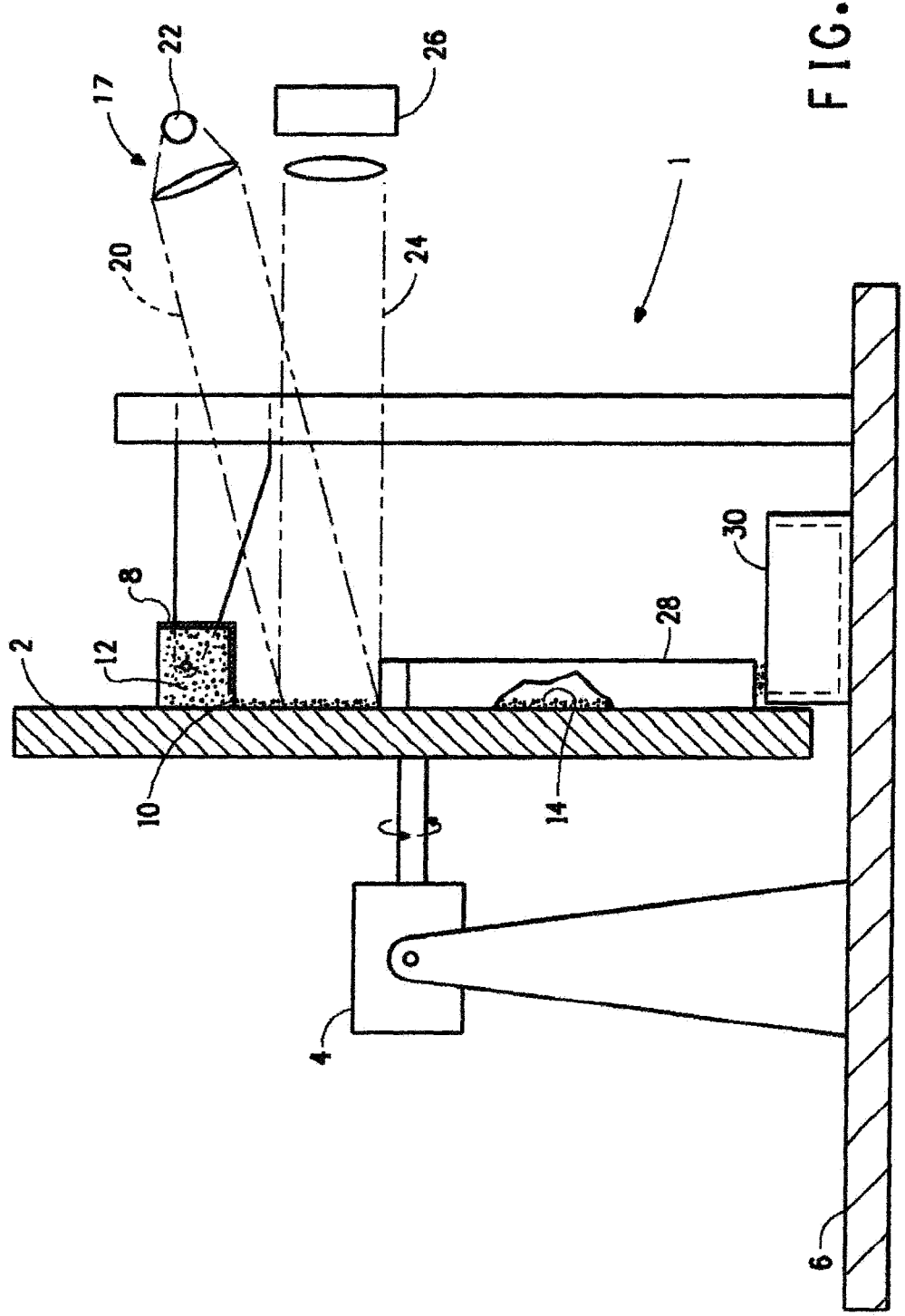

One of the flop prediction devices suitable for the process of the present invention includes a device 1 shown in FIGS. 1 and 2. Device 1 includes a test substrate 2, preferably a disc, rotated by a driver 4, such as an electric motor, which is positioned on a support frame 6. Test substrate 2 mounted on a shaft of driver 4 can be positioned either in a horizontal or in a vertical position. Test substrate 2 of device 1 shown in FIGS. 1 and 2 is positioned vertically, which is preferred. Test substrate 2 can be made of any suitable material, such as steel, plastic or aluminum. The surface of test substrate 2 preferably has the same degree of smoothness as that of, for example, auto body or auto bumper such that the results obtained are as close to those that would have been obtained under the similar paint application conditions.

As shown in FIG. 1, Device 1 is provided with a vessel 8 positioned adjacent to test substrate 2. Vessel 8 is provided with an opening 10, preferably a slot, through which a coating composition ($S_0$) 12, when poured into vessel 8, can be applied as a $L_0$ layer 14 of a substantially uniform thickness on a measurement area 16 on the surface of test substrate 2. Coating composition ($S_0$) 12 used in producing $L_0$ layer 14 is free from or substantially free from a rheology additive. As test substrate 2 is rotated by driver 4, preferably for about a quarter turn, $L_0$ layer 14 is created. Opening 10 is adjacent to substrate 2 such that a resulting gap between opening 10 and substrate 2 controls the thickness of $L_0$ layer. Typically, $L_0$ layer is provided with a thickness that ranges from 6 micrometers to 2300 micrometers.

Mottling prediction device 1 of the present invention includes a conventional optical measurement mechanism 17 provided with conventional collimators for producing a beam of light 20 of preset intensity at a preset angle that can be projected on measurement area 16 from a conventional light source 22. A $B_0$ flop 24 of beam of light 20 off of $L_0$ layer 14 can then be measured by a conventional optical measurement instrument 26, such as multi-angle spectrophotometer or a multi-angle colorimeter. One suitable optical measurement instrument can be MA-68 flop measurement device supplied by X-Rite of Grandville, Mich. Any angle of incidence and angles of reflectance can be used. However, a 45 degree angle of incidence from a specular direction is typically employed and reflectance preferably at 15 and 110 degree angles of reflection is measured before there is substantial change in the optical characteristics of $L_0$ layer 14 that depend on the physical and chemical properties of the coating composition from which $L_0$ layer 14 is produced. Thus, the higher the content of the solvent in the coating composition, the longer would be the window during which the flop can be measured and vice versa. Coating compositions that are lacquers (those containing high molecular weight non-reactive binder polymers dissolved in a solvent) typically would have longer measurement window than coating compositions that are enamels (those containing binder polymers containing reactive groups that chemically react with crosslinking groups on crosslinking agents that are mixed before being applied as a layer on a substrate). Typically, the flop is measured substantially immediately as practical or within 2 seconds to 15 seconds after $L_0$ layer 14 is applied over test substrate 2.

Applicants made an unexpected discovery that the flop of a wet layer of a coating composition free from rheology additive tends to drop over time whereas the flop of a wet layer of a coating composition containing rheology additive tends to stay substantially constant over time and no noticeable drop in flop occurs. Additionally, applicants also made an unexpected discovery that as the amount of rheology additive added to the coating composition is increased; the delta flop of a wet layer of that coating composition tends to be smaller. Thus, the higher the amount of rheology additive added to the coating composition, the less would be the drop in flop over same time period. Applicants have applied this unexpected discovery to determine the degree of mottling exhibited in a coating that resulting from a coating composition by measuring the drop in flop over time. By trial and error, it is possible to determine a desired time interval after which the drop on flop can be measured. The desired time interval can be affected by the type and amount of rheology additive present as well as the type and amount of solvents, binders, pigment volume loading (PVC) in the coating composition as well as the thickness of the layer applied over a substrate. The desired time interval can typically range from 5 seconds to 60 seconds.

Thus, after the aforedescribed time interval, beam of light 20 of the preset intensity at the preset angles can be projected on measurement area 16 and $B_{H0}$ flop 24 of beam of light 20 off of $L_0$ layer 14 can then be measured by an optical measurement device 26, such as multi-angle spectrophotometer or a multi-angle colorimeter. Any angle of incidence and reflectance can be used. However, a 45 angle from a specular direction is typically employed and is preferably measured before there is substantial change in the optical characteristics of $L_0$ layer 14 that depend on the physical and chemical properties of the coating composition from which $L_0$ layer 14 is produced. If desired, conventional light source 22 can be positioned within the optical measurement device 26.

Means for configuring computer readable program code devices is used to cause a conventional computer to store $B_0$ flop and $B_{H0}$ flop 24 of $L_0$ layer 14 in a computer usable storage medium of the computer (not-shown in FIG. 1). The computer is preferably in communication with optical measurement device 26. If desired, the computer can be in communication with a remote computer, such as an offsite computer used to gather information from one or more computers connected to mottling prediction devices of the present invention.

Then, $L_{H0}$ layer is dried and/or cured into a $C_0$ coating resulting from $S_0$ coating composition and its degree of mottling $Y_0$ is measured by means, such as the visual observation process described in a brochure published on Nov. 17, 2010 by BASF Chemical Company entitled "Color homogeneity (mottling) of effect basecoats by Dr. Dirk Eierhoff and Georg Wigger of BASF Coating GmbH (hereinafter BASF Process), which is incorporated herein by reference. The degree of mottling $Y_0$ is visually assessed by the aforedescribed BASF Process on a scale of 1 to 5 with 1 being free from mottling, 2 being actable mottling and 5 being strong mottling.

If desired, after $B_{H0}$ flop of $L_0$ layer is measured, substrate 2 can be rotated further by driver 4 to scrape off the coating with a doctor blade 28 into a waste container 30 and substrate 2 can then be cleaned. Alternatively, after $B_{H0}$ flop is measured, substrate 2 can be removed; $L_0$ layer scraped off of substrate 2 and then substrate 2 is cleaned for the next step.

Alternatively, simultaneously, prior to, or in conjunction therewith, a layer substantially identical $L_0$ layer from $S_0$ coating composition can be applied over an identical substrate and its degree of mottling $Y_0$ can be visually assessed by the aforedescribed visual observation process on a scale of 1 to 5.

The aforedescribed procedure is then repeated with series of $S_1, S_2, \ldots S_n$ (n ranges 1 to 100, preferably from 2 to 50 and more preferably from 5 to 20) coating compositions 12 containing increasing amounts one or more rheology additives ranging from $F_1$ to $F_n$ weight parts per 100 weight parts of coating composition. The increasing amount of rheology additives added to the coating composition can be preferably increased in suitable set amounts, such as 0.001, 0.01, 0.1, 0.5, 1, 5, 10, 15 weight parts in per 100 weight parts of the coating composition, with $F_0$ ranging from 0.001 weight part to 5 weight parts per 100 weight parts of the coating composition and $F_n$ ranging from 5.1 weight parts to 60 weight parts per 100 weight parts of coating composition. As described above, $B_1$ flop 24 from a $L_1$ layer 14, $B_{H1}$ flop 24 from a $L_1$ layer 14 from $S_1$ coating composition after the desired time interval are measured and along with degree of mottling $Y_1$ are measured. The process is repeated till $B_n$, $B_{Hn}$ flops 24 from $L_n$ layer 14 from $S_n$ coating composition 12 along with degree of mottling $Y_n$ are measured. Then, the means for configuring computer readable program code devices is used to cause the computer to subtract $B_{H0}$ to $B_{Hn}$ flops from $B_0$ to $B_n$ flops, respectively of $L_0$ to $L_n$ layers to determine $\Delta B_0$ to $\Delta B_n$ flops.

Then, the means for configuring computer readable program code devices is used to cause the computer to store $B_0$ flop, $B_1$ to $B_n$ flops, $B_{H0}$ to $B_{Hn}$ flops 24 and $\Delta B_0$ to $\Delta B_n$ flops of $L_0$ to $L_n$ layers 14, respectively, and degree of mottling $Y_0$ to $Y_n$, respectively of $C_0$ to $C_n$ coatings in the computer usable storage medium of the computer. It should be understood that the sequence in which the foregoing measurements are stored the computer usable storage medium of the computer is not critical to the process of the invention.

The means for configuring computer readable program code devices is used to cause the computer to locate intersecting points on a graph where $\Delta B_0$ to $\Delta B_n$ flops of $L_0$ to $L_n$ layers 14 on X-axis of the graph intersect with the degree of mottling $Y_0$ to $Y_n$, respectively of $S_0$ to $S_n$ coating compositions, on Y-axis of the graph. The means for configuring computer readable program code devices is then used to cause the computer to use a curve fitting equation to produce a mottling prediction curve on the graph. Preferably, the curve fitting equation is a second degree polynomial equation. More preferred second degree polynomial equation is of the following formula:

$$\text{Degree of mottling } Y_n = a(\Delta B_n)^2 + b(\Delta B_n) + c \qquad (1)$$

$$R^2 = Z \qquad (2)$$

wherein said constants a, b, c and $R^2$ are determined by a curve fitting process, such as that described in Microsoft Office Excel® 2003 supplied by Microsoft Corporation of Redmond, Wash. Z is a statistical measure of how close the curve fits to the experimental datum points on a graph. When Z is equal to 1, it is considered to be an ideal fit, i.e., all the experimental datum points lay on the fit curve. All the necessary and relevant information can be stored on the computer usable storage medium.

If desired, the mottling prediction curve on the graph may be displayed on a conventional monitor and/or printed on paper by means of a conventional printer both of which being in communication with the computer. Once the mottling prediction curve on the graph is produced, the user can use the mottling prediction device of the present invention to predict the degree of mottling of a target coating composition containing an unknown or known amount of one or more rheology additives without going through the cumbersome and time consuming process of curing the layer into a coating. $L_T$ layer 14 (also know as target layer) from the target coating composition, preferably having the compositional element and preferably having the same substantially uniform thickness as the layers used in creating the mottling prediction curve, dispensed over substrate 2 of mottling prediction device 1 of the present invention can be used in a production set up that allows the manufacturer of a coating composition to expeditiously adjust the ingredients of the coating composition for ensuring that the resulting coating composition has a desired degree of mottling.

As described above, $B_T$ flop 24 from $L_T$ layer 14 from the target coating composition is measured and the means for configuring computer readable program code devices is used to cause the computer to store $B_T$ flop 24 of $L_T$ layer 14 in the computer usable storage medium of the computer. Thereafter, $B_{HT}$ flop 24 from $L_T$ layer 14 from the target coating composition is measured after the same desired time interval as that used in crating the aforedescribed mottling prediction curve. The means for configuring computer readable program code devices is used to cause the computer to subtract the $B_{HT}$ flop 24 of $L_T$ layer 14 from $B_T$ flop 24 of $L_T$ layer 14 to determine $\Delta B_T$ flop of $L_T$ layer 14.

The means for configuring computer readable program code devices is used to cause the computer to locate $\Delta B_T$ flop of $L_T$ layer on the X-axis of the graph. The means for configuring computer readable program code devices is used to cause the computer to locate an intersecting point on the mottling prediction curve that intersects with $\Delta B_T$ on X-axis of the graph. Finally, The means for configuring computer readable program code devices is used to cause the computer to predict the mottling of a target coating resulting from $L_T$ layer by locating $Y_T$ degree of mottling on the Y-axis of the graph that intersects with the intersecting point on the flake amount prediction curve that intersects with $B_T$ on the X-axis of the graph.

As a result, once the flake amount prediction curve is stored in a computer of device 1, an aliquot of a coating composition being made can be applied as a layer and its $\Delta B_T$ flop measured to predict the degree of mottling of said composition. If the amount measured falls outside of desired specification, the manufacturing process can be adjusted without interruption by monitoring the degree of mottling on a continuing basis.

Few of the aspects of the aforedescribed flop prediction device 1 of the present invention are described in German patent application DT 25 25 701 A1. It should be understood that substrate 2 need not be positioned vertically or have to have a disc shape. Other embodiments, such as those where substrate is positioned horizontally, or is in the form of a belt, etc. are also well suited for the process of the present invention. For example, substrate in the form of a roller, as described in a commonly assigned U.S. Pat. No. 6,583,878 to Hustert, is also well suited for the process of the present invention.

One embodiment of the process of the present invention utilizes mottling prediction device 1 of FIG. 1. The process includes dispensing on substrate 2, $L_0$ layer 14 of a substantially uniform thickness of coating composition 12 through vessel 8, which contains containing coating composition 12. Then beam of light 20 of a preset intensity at preset angles of incidence from light source 22 is projected on measurement area 16 of $L_0$ layer. By means of optical measurement device 26, $B_0$ flop of beam of light 20 is measured at preset angles of reflectance. $B_0$ flop of $L_0$ layer is then stored in the computer usable storage medium of the computer. After a desired time interval, $B_{H0}$ flop of beam of light 20 is measured at preset angles of reflectance and then stored in the computer usable storage medium of the computer, and the means for configuring computer readable program code devices is used to cause the computer to subtract $B_{H0}$ flop of $L_0$ layer from $B_0$ flop to determine $\Delta B_0$. Then, $L_0$ layer is allowed to dry and/or cure into $C_0$ coating and its degree of mottling is visually assessed by the procedure described earlier. The aforedescribed steps are repeated for $S_1$ to $S_n$ coating compositions 12 further comprising $F_1$ to $F_n$ parts by weight of one or more rheology additives based on 100 parts by weight of the coating composition respectively to determine $B_1$ to $B_n$ flops of $L_1$ to $L_n$ layers wherein n ranges 1 to 100, preferably from 2 to 50 and more preferably from 5 to 20 $B_{H1}$ to $B_{Hn}$ flops 24 and $\Delta B_0$ to $\Delta B_n$ flops of $L_0$ to $L_n$ layers 14, respectively, and the degree of mottling $Y_0$ to $Y_n$, respectively of $C_0$ to $C_n$ coatings. Then, the means for configuring computer readable program code devices is used to cause the computer to store $B_0$ flop, $B_1$ to $B_n$ flops, $B_{H1}$ to $B_{Hn}$ flops 24 and $\Delta B_0$ to $\Delta B_n$ flops of $L_0$ to $L_n$ layers 14, respectively, and the degree of mottling $Y_0$ to $Y_n$, respectively of $C_0$ to $C_n$ coatings in the computer usable storage medium of the computer.

EXAMPLES

The samples were prepared by adding to Imron® 701P polymer (P) supplied by DuPont Company of Wilmington, Del., various amounts of BYK®-411 to rheology additive (RA) supplied by BYK USA Inc. of Wallingford, Conn. in the amounts shown below in Table 1. Wet layers 14 of these samples were applied over substrate 2 of Device 1 and flops 24 of the layers was measured using MA-68 color instrument 26 supplied by X-Rite of Grand Rapids, Mich. by the aforedescribed mottling prediction process and mottling prediction device was measured by the mottling prediction device of the present invention at the start and then after time T of approximately 200 sec. The degree of mottling of a coating resulting after cure was measured by activating the mixers with VG-6005 activator supplied by DuPont Company of Wilmington, Del. at 4:1 volume ratio and sprayed by pressure pot spray (RP 1.3 mm tip from SATA, Domertalstr. 20-70806 Kornwestheim, Germany). After 24 hour cure at 20° C. (50% humidity), the degree of mottling was evaluated by the aforedescribed BASF Process.

TABLE 1

| Ex. | P in grams | RA in grams | Flop at start | Flop after time t | Delta flop | Degree of mottling |
|---|---|---|---|---|---|---|
| A | 100 | 0.0 | 2.88 | 0.02 (196 sec.) | 2.86 | 1 |
| B | 99.9 | 0.1 | 2.90 | 2.00 (195 sec.) | 0.9 | 2 |
| C | 99.8 | 0.2 | 2.90 | 2.50 (195 sec.) | 0.5 | 3 |
| D | 99.7 | 0.3 | 2.90 | 2.93 (200 sec.) | 0.03 | 5 |

Figure 3:
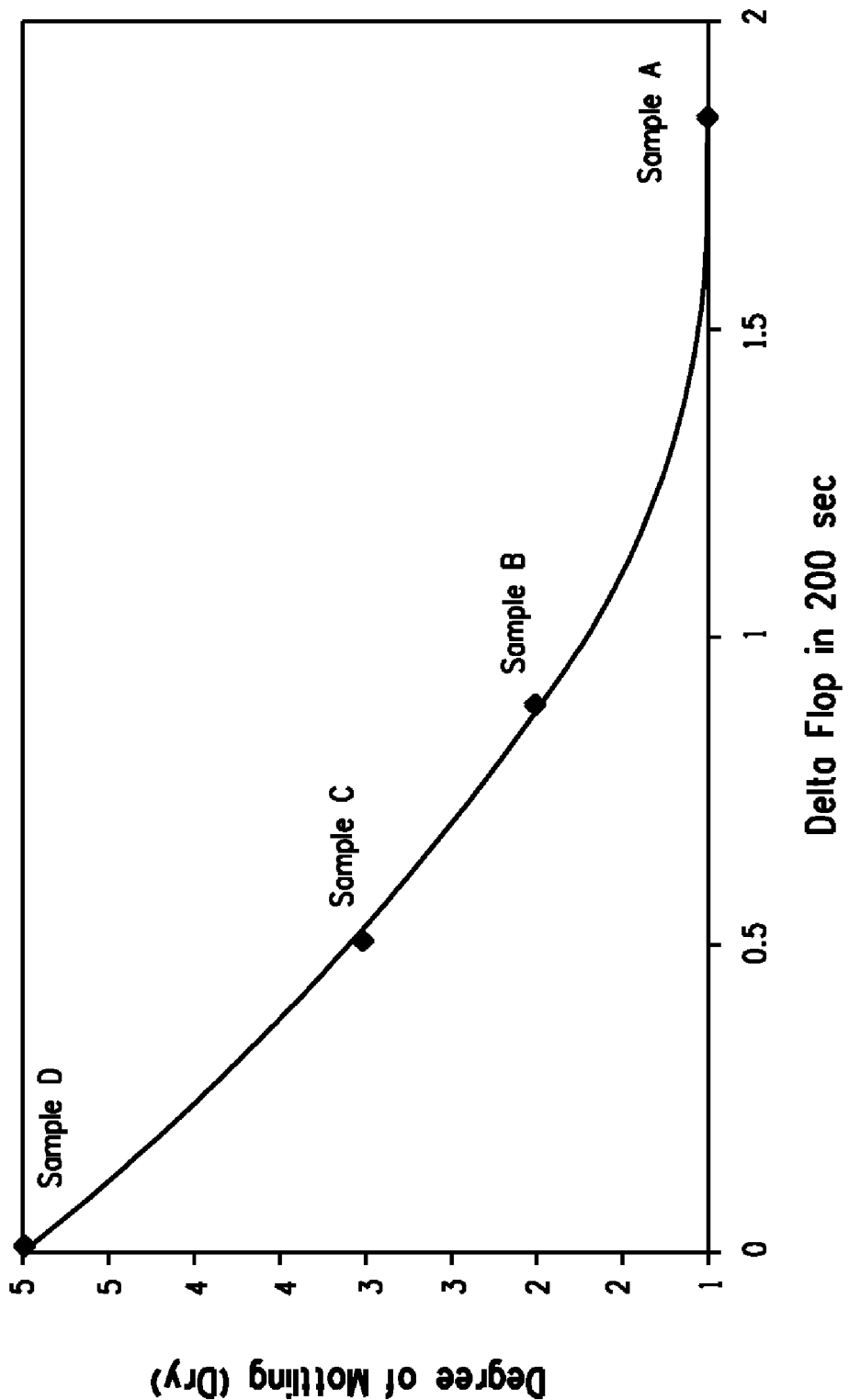
FIG. 3 broadly illustrates the mottling prediction curve produced by the mottling prediction device of the present invention.

The aforedescribed delta flop and the degree of flop were plotted by the process described earlier to produce the mottling prediction curve shown in FIG. 3. As shown in FIG. 3, intersecting points on a graph where $B_0$ to $B_n$ of $L_0$ (Ex. A) to $L_n$ (Ex. D) layers on X-axis of the graph intersect with the degree of mottling of $S_0$ to $S_n$ coating compositions on Y-axis of the graph are then located.

Using a curve fitting equation, such as the aforementioned secondary degree polynomial equation (1) is then used to produce a flop amount prediction curve, such as that shown in FIG. 3. The term "a" in the equation (1) was 1.3739. The term "b" in the equation (1) was −4.7635 and the term "c" in the equation was 5.1153. The statistical measure Z was 0.9988. All of the foregoing terms were obtained by using the aforementioned Microsoft Excel® program. It would be readily to apparent to one of ordinary skill in the art that the statistical measure Z of 0.9988 indicates the curve of the mottling prediction was very close fit to the Z of the ideal fit of 1.

The process of the present invention is then used to predict the degree of mottling of a target coating composition by first dispensing on substrate 2 a $L_T$ layer of preferably the same substantially uniform thickness of a target coating composition through vessel 8 of flop amount prediction device 1 containing the target coating composition further comprising an unknown or a known amount of the rheology additive. A beam of light 20 at the preset intensity and at the preset angles of incidence from light source 22 is then projected on measurement area 16 of $L_T$ layer and $B_T$ flop of beam reflected from $L_T$ layer at the preset angles of reflectance is measured by optical measurement device 26 followed by $B_{HT}$ flop of beam reflected from $L_T$ layer after the desired time interval, which is the same as that used in creating the mottling prediction curve. An intersecting point on the mottling prediction curve that intersects with $\Delta B_T$ flop ($B_T$–$B_{HT}$) on the X-axis of said graph is then located and the degree of mottling at the preset flop angles of a coating resulting from $L_T$ layer is then predicted by locating $Y_T$ on the Y-axis of the graph.

Thus, one of ordinary skill in the art can readily see that the degree of mottling can be readily predicted by the mottling prediction curve of the process of the present invention by just measuring the delta flop of a wet layer of a coating composition.

The process and device of the present invention is most suitable for predicting the degree mottling of automotive OEM and refinish paints during their manufacture

What is claimed is:

1. A process for predicting degree of mottling in a target coating composition comprising:
   (a) adding to a vessel of a mottle prediction device a $S_0$ coating composition;
   (b) dispensing from an opening in said vessel said $S_0$ coating composition over a test substrate to produce a $L_0$ layer of a substantially uniform thickness thereon;
   (c) projecting on said $L_0$ layer a beam of light of a preset intensity at preset angles of incidence from a light source;
   (d) measuring $B_0$ flop of said beam reflected from said $L_0$ layer at preset angles of reflectance by an optical measurement instrument;
   (e) measuring $B_{H0}$ flop of said beam reflected from said $L_0$ layer at preset angles of reflectance by said optical measurement instrument after a desired time interval;
   (f) producing a $C_0$ coating from said $S_0$ coating composition;
   (g) assessing a degree of mottling $Y_0$ of said $C_0$ coating;
   (h) repeating said steps (a) through (g) for $S_1$ to $S_n$ coating compositions respectively comprising $F_1$ to $F_n$ parts by weight of one or more rheology additives based on 100 parts by weight of said $S_1$ to $S_n$ coating compositions to determine $B_1$ to $B_n$ flops and $B_{H1}$ to $B_{Hn}$ flops of $L_1$ to $L_n$ layers after said desired time interval, respectively, and degree of mottling $Y_1$ to $Y_n$ of $C_1$ to $C_n$ coatings, respectively wherein n ranges from 1 to 100;
   (i) subtracting said $B_{H0}$ to $B_{Hn}$ flops from said $B_0$ to $B_n$ flops of said $L_0$ to $L_n$ layers, respectively to determine $\Delta B_0$ to $\Delta B_n$ flops;
   (j) storing said $B_0$ to $B_n$ flops, said $B_{H0}$ to $B_{Hn}$ flops, said $\Delta B_0$ to $\Delta B_n$ flops and said degree of mottling $Y_0$ to $Y_n$ in a non-transitory computer usable storage medium of a computer;
   (k) locating intersecting points on a graph where said $\Delta B_0$ to $\Delta B_n$ flops of said $L_0$ to $L_n$ layers on X-axis of said graph intersect with said degree of mottling $Y_0$ to $Y_n$ on Y-axis of said graph;
   (l) using a curve fitting equation to produce a degree of mottling prediction curve on said graph;
   (m) dispensing on said test substrate a $L_T$ layer of said substantially uniform thickness of a target coating composition from said vessel wherein said target coating composition contains flakes;
   (n) projecting on said $L_T$ layer a beam of light at said preset intensity and at said preset angles of incidence from said light source;
   (o) measuring $B_T$ flop of said beam reflected from said $L_T$ layer at said preset angles of reflectance by said optical measurement instrument;
   (p) measuring $B_{HT}$ flop of said beam reflected from said $L_T$ layer at preset angles of reflectance by said optical measurement instrument after said desired time interval;
   (q) subtracting said $B_{HT}$ flop from said $B_T$ flop of said $L_T$ layer to determine $\Delta B_T$ flop;
   (r) locating said $\Delta B_T$ flop of said $L_T$ layer on said X-axis of said graph;
   (s) locating an intersecting point on said degree of mottling prediction curve that intersects with said $\Delta B_T$ flop on said X-axis of said graph; and
   (t) predicting degree of mottling of said target composition by locating $Y_T$ on said Y-axis of said graph that intersects with said intersecting point on said degree of mottling prediction curve that intersects with said $\Delta B_T$ on said X-axis of said graph.

2. The process of claim 1 wherein said optical measurement instrument is a multi-angle spectrophotometer or a multi-angle colorimeter.

3. The process of claim 1 wherein said optical measurement instrument is in communication with said computer.

4. The process of claim 1 wherein said flakes having a size ranging from 25 microns to 2000 microns.

5. The process of claim 1 wherein said opening is a slot adjacent to said test substrate such that a resulting gap between said slot and said test substrate controls the thickness of said $L_0$ to $L_n$ layers.

6. The process of claim 1 wherein said $L_0$ to $L_n$ layers are of the same thickness ranging from 6 micrometers to 2300 micrometers.

7. The process of claim 1 wherein said test substrate is a disc positioned substantially vertically on a support frame of said mottle prediction device.

8. The process of claim 1 wherein said curve fitting equation is a second degree polynomial equation.

9. The process of claim 8 wherein said second degree polynomial equation is of the formula:

Degree of mottling $Y_n = a(\Delta B_n)^2 + b(\Delta B_n) + c$ $R^2 = Z$ wherein said constants a, b, c and Z are determined by a curve fitting process.

10. The process of claim 1 comprising displaying said predicted amount of said flakes contained in said target coating composition on a CRT monitor.

11. The process of claim 1 comprising communicating said predicted amount of said flakes contained in said target coating composition from said computer to a remote computer.

12. The process of claim 1 wherein said target coating composition is an automotive OEM or refinish paint.

13. The process of claim 1 wherein said flakes are aluminum flakes, interference flakes, inorganic flakes, organic flakes or a combination thereof.

* * * * *